(12) United States Patent
McKay

(10) Patent No.: US 9,163,212 B2
(45) Date of Patent: Oct. 20, 2015

(54) OSTEOGENIC CELL DELIVERY MATRIX

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 295 days.

(21) Appl. No.: 12/692,940

(22) Filed: Jan. 25, 2010

(65) Prior Publication Data

US 2011/0182961 A1    Jul. 28, 2011

(51) Int. Cl.
| | |
|---|---|
| A61K 9/14 | (2006.01) |
| A61K 33/42 | (2006.01) |
| A61K 47/02 | (2006.01) |
| A61K 35/12 | (2015.01) |
| A61P 19/00 | (2006.01) |
| C12N 5/00 | (2006.01) |
| A61L 27/42 | (2006.01) |
| A61L 27/56 | (2006.01) |

(52) U.S. Cl.
CPC .............. *C12N 5/0068* (2013.01); *A61L 27/425* (2013.01); *A61L 27/56* (2013.01); *C12N 2533/14* (2013.01)

(58) Field of Classification Search
CPC ......... A61L 27/02; A61L 27/42; A61L 27/56; A61K 9/14; A61K 33/42; A61K 47/02
USPC ................................. 424/423, 489, 484, 602
See application file for complete search history.

(56) References Cited

U.S. PATENT DOCUMENTS

| | | | |
|---|---|---|---|
| 5,549,904 A | 8/1996 | Juergensen et al. | |
| 6,018,095 A * | 1/2000 | Lerch et al. | 128/898 |
| 6,863,900 B2 | 3/2005 | Kadiyala et al. | |
| 2003/0009235 A1 | 1/2003 | Manrique et al. | |
| 2008/0033572 A1* | 2/2008 | D'Antonio et al. | 623/23.51 |
| 2009/0028770 A1* | 1/2009 | Mae et al. | 423/304 |
| 2009/0104164 A1 | 4/2009 | Zhang et al. | |
| 2009/0149569 A1 | 6/2009 | Shastri et al. | |

FOREIGN PATENT DOCUMENTS

WO    WO 02/070029 A3 * 9/2002

OTHER PUBLICATIONS

Purich et al. (Handbook of Biochemical Kinetics, p. 107).*
Oliveira et al. (Biomaterials, 27, Published 2006, pp. 6123-6137).*
Moroni et al. (PLoS One, Regenerating Articular Tissue by Converging Technologies, vol. 3, Issue 8, Published Aug. 21, 2008, pp. 1-10).*
BD Biosciences (BD Matrigel matrix Frequently asked questions pp. 1-7, Accessed on Dec. 13, 2013, http://www.bdbiosciences.com/documents/BD_CellCulture_Matrigel_FAQ.pdf.).*
Moroni et al. (PLoS One, Regenerating Articular Tissue by Converging Technologies, vol. 3, Issue 8, Published Aug. 21, 2008, pp. 1-10, Supporting Information Table S2 Pore size and porosity distribution of the single components and of the final scaffold constructs.doi:10.1371/journal.pone.0003032.s002.*
International Search Report and Written Opinion for PCT/US2011/022413 the counterpart application mailed on Oct. 27, 2011.
T. Livingston et al., A comparative study of biphasic calcium phosphate ceramics for human mesenchymal stem-cell-induced bone formation, Original Research Article, Biomaterials Jun. 2005, vol. 26, pp. 3631-3638, abstract.
Q. Wang et al., Clinical orthopaedics and related research, No. 348, pp. 259-268, abstract.
Toquet et al., Osteogenic potential in vitro of human bone marrow cells cultured on macroporous biphasic calcium phosphate ceramic, 1999, pp. 98-108, abstract.
W. Lind et al., Factors stimulating bone formation, Eur Spine J. 2001, vol. 10, S102-S109, See S103, right column, Line 17-30.
European Search Report for PCT/US2011/022413 the counterpart application mailed on Aug. 27, 2013.
Hua Zhang et al: "Preparation and biocompatibility evaluation of apatite/wollastonite-derived porous bioactive glass ceramic scaffolds; Preparation and biocompatibility evaluation of A/W porous bioactive glass ceramic scaffolds", Biomedical Materials, Institute of Physics Publishing, Bristol, GB, vol. 4, No. 4, Aug. 1, 2009, p. 45007, XP020163016, ISSN: 1748-605X* 2.1 Fabrication of a porous bioactive glass ceramic scaffold ** 2.4.2 Cell culture and cell seeding*.
Yoshiyuki Ito et al: "Bone formation using novel interconnected porous calcium hydroxyapatite ceramic hybridized with cultured marrow stromal stem cells derived from Green rat", Journal of Biomedical Materials Research, vol. 69A, No. 3, Jun. 1, 2004, pp. 454-461, XP055075321, ISSN: 0021-9304, DOI: 10.1002/jbm.a.30014 * Materials and Methods: Interconnective porous calcium hydroxyapatite ceramic (IP-CHA)** Materials and Methods: MSCs preparation and hybridization to IP-CHA *.
Guangpeng Liu et al: "Tissue-engineered bone formation using human bone marrow stromal cells and novel [beta]-tricalcium phosphate. This work was supported by the National Basic Research Program of China (G1999054300, 2005CB522700) and Shanghai Science and Technology Development Foundation.; Tissue-engineered bone formatio", Biomedical Materials, Institute of Physics Publishing, Bristol, GB, vol. 2, No. 2, Jun. 1, 2007, pp. 78-86, XP020125610, ISSN: 1748-605X, DOI.
Suvi Haimi et al: "Growth and Osteogenic Differentiation of Adipose Stem Cells on PLA/Bioactive Glass and PLA/[beta]-TCP Scaffolds", Tissue Engineering Part A, vol. 15, No. 7, Jul. 1, 2009, pp. 1473-1480, XP055075453, ISSN: 1937-3341, DOI:10.1089/ten.tea.2008. 0241 *Materials and Methods: Materials fabrication **Materials and Methods: Cell Seeding and culture of ASC-seeded composite scaffold *.
Arinzeh T L et al: "A comparative study 1 of biphasic calcium phosphate ceramics for human mesenchymal stem-cell-induced bone formation", Biomaterials, Elsevier Science Publishers BV., Barking, GB, vol. 26, No. 17, Jun. 1, 2005, pp. 3631-3638, XP027767979, ISSN: 0142-9612 [retrieved on Jun. 1, 2005]* 2.1 Ceramics ** 2.2 Human mesenchymal stem cell isolation and seeding *.

(Continued)

Primary Examiner — Johann R Richter
Assistant Examiner — Alma Pipic
(74) Attorney, Agent, or Firm — Sorell Lenna & Schmidt LLP

(57) ABSTRACT

Compositions and methods for augmenting bone formation by administering isolated human mesenchymal stem cells (hMSCs) within a matrix provided. By adding calcium and/or phosphate ions to the matrix, one may foster greater bone regeneration.

11 Claims, No Drawings

(56) References Cited

OTHER PUBLICATIONS

Thein-Han W Wet al: "Biomimetic chitosan-nanohydroxyapatite composite scaffolds for bone tissue engineering", ACTA Biomaterialia, Elsevier, Amsterdam, NL, vol. 5, No. 4, May 1, 2009, pp. 1182-1197, XP026051893, ISSN: 1742-7061, DOI: 10.1016/J. ACTBIO.2008.11.025 [retrieved on Apr. 15, 2009] * the whole document *.

Kong L et al: "preparation and characterization of nano-hydroxyapatite/chitosan composite scaffolds", Journal of Biomedical Materials Research, Wiley, New York, NY, US, vol. 75A, No. 2, Nov. 1, 2005, pp. 275-282, XP002608051, ISSN: 0021-9304, DOI: 10.1002/JBM.A.30414 [retrieved on Jul. 25, 2007] * the whole document *.

Ander Abarrategi et al: "Improvement of Porous [beta]-TCP Scaffolds with rhBMP-2 Chitosan Carrier Film for Bone Tissue Application", Tissue Engineering Part A, vol. 14, No. 8, Aug. 1, 2008, pp. 1305-1319, XP055075454, ISSN: 1937-3341, DOI: 10.1089/ten.tea.2007.0229 * the whole document *.

Shu-Hua Yang et al: "Tricalcium phosphate and glutaraldehyde crosslinked gelatin incorporating bone morphogenetic protein-A viable scaffold for bone tissue engineering", Journal of Biomedical Materials Research Part B: Applied Biomaterials, vol. 74B, No. 1, Jul. 1, 2005, pp. 468-475, XP055075455, ISSN: 1552-4973, DOI: 10.1002/jbm.b.30200 * the whole document*.

Isao Hirata et al: "Acceleration of bone formation with BMP2 in frame-reinforced carbonate apatite-collagen sponge scaffolds", Journal of Artificial Organs; The Official Journal of the Japanese Society for Artificial Organs, Springer-Verlag, TO, vol. 10, No. 4, Dec. 20, 2007, pp. 212-217, XP019545415, ISSN: 1619-0904, DOI: 10.1007/S10047-007-0391-2 * the whole document *.

Chao Zhang et al: "A study on a tissue-engineered bone using rhBMP-2 induced periosteal cells with a porous nano-hydroxyapatite/collagen/poly(L-lactic acid) scaffold; A study on a tissue-engineered bone using rhBMP-2 induced periosteal cells with a porous nano-HA/collagen/PLA scaffold", Biomedical Materials, Institute of Physics Publishing, Bristol, GB. vol. 1, No. 2, Jun. 1, 2006, pp. 56-62, XP020111447, ISSN: 1748-605X, DOI: 10.1088/1748-6041/1/2/002 * the whole document *.

Takahashi Y et al: "Enhanced osteoinduction by controlled release of bone morphogenetic protein-2 from biodegradable sponge composed of gelatin and beta-tricalcium phosphate", Biomaterials, Elsevier Science Publishers BV., Barking, GB, vol. 26, No. 23, Aug. 1, 2005, pp. 4856-4865, XP027768289, ISSN: 0142-9612 [retrieved on Aug. 1, 2005] * the whole document *.

* cited by examiner

OSTEOGENIC CELL DELIVERY MATRIX

BACKGROUND

Bone is a composite material that contains impure hydroxyapatite, collagen and a variety of non-collagenous proteins, as well as embedded and adherent cells. Due to disease, a congenital defect or an accident, a person may lose or be missing part or all of one or more bones or regions of cartilage in his or her body, and/or have improper growth or formation of bone and/or cartilage.

That an organism is missing part of a bone or has a defect is not necessarily a permanent condition, and there are known means by which to address some of these conditions. For example, mammalian bone tissue is known to contain one or more proteinaceous materials that are active during growth and natural bone healing. These materials can induce a developmental cascade of cellular events that results in bone formation. Typically, the developmental cascade of bone formation involves chemotaxis of mesenchymal cells, proliferation of progenitor cells, differentiation of cartilage, vascular invasion, bone formation, remodeling and marrow differentiation. Thus, the control or use of this already existing system can be advantageous when seeking to regenerate or to repair bone.

In order to facilitate regrowth of bone, it can be advantageous to include or to co-administer stem cells. Stem cells may, for example, be introduced when inserting an implant. Unfortunately, the full potential of stem cells to regenerate tissue or bone has not been reached. The present invention is directed toward increasing the efficacy of stem cell applications.

SUMMARY

Implants and matrices are provided that improve osteogenesis. By using a matrix that contains calcium and/or phosphate ions and stem cells, efficient and effective osteogenesis may be achieved. Thus, there are methods and compositions for directing stem cells that are, for example, cultivated in vitro, in vivo or ex vivo to differentiate into specific cell lineage pathways prior to, at the time of, or following, their implantation for the therapeutic treatment of elective procedures or pathologic conditions. These conditions may be in humans, other primates or other mammals.

In some embodiments, the compositions provided increase the ability of stem cells to generate bone and/or cartilage growth.

In some embodiments, an implantable matrix is provided that is configured to fit at or near a target tissue site, the matrix comprising: calcium and/or phosphate ions and stem cells.

In some embodiments, an implantable matrix configured to fit at or near a target tissue site is provided, the matrix comprising: a porous ceramic, calcium and/or phosphate ions and stem cells.

In some embodiments, there is a method of treating a bone defect in which the bone defect site possesses at least one cavity. The method comprises inserting a collagen matrix into the defect, the collagen matrix optionally comprising a plurality of ceramic particles embedded within the collagen. The matrix also comprises calcium and/or phosphate ions and stem cells and allows influx of progenitor, bone and/or cartilage cells therein. In some embodiments, the matrix comprises bone morphogenic protein.

In some embodiments, there is a method for augmenting bone formation in an individual in need thereof by administering isolated human mesenchymal stem cells associated with a matrix that supports the differentiation of the stem cells into osteogenic lineages to an extent sufficient to generate bone formation therefrom. The matrix may, for example, be selected from a ceramic and a resorbable biopolymer or a combination thereof. The ceramic may, for example, be in particulate form or in the form of a structurally stable, three dimensional implant, such as a cube, cylinder, block or appropriate anatomical form. The matrix may comprise ceramic granules dispersed within or on the matrix. In some embodiments, the biopolymer is a matrix containing gelatin, collagen, keratin, chitosan, or cellulose or combinations thereof and can be in the form of a powder or sponge. An example of a type of collagen is a type I bovine collagen derived from skin. The matrix also contains calcium and/or phosphate ions.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations; the numerical values are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Additionally, unless defined otherwise or apparent from context, all technical and scientific terms used herein have the same meanings as commonly understood by one of ordinary skill in the art to which this invention belongs.

Unless explicitly stated or apparent from context, the following terms or phrases have the definitions provided below:

Definitions

It is noted that, as used in this specification and the appended claims, the singular forms "a," "an," and "the," include plural referents unless expressly and unequivocally limited to one referent. Thus, for example, reference to "a matrix" includes one, two, three or more matrices.

The term "allograft" as utilized herein refers to tissue intended for implantation that is taken from a different member of the same species as the intended recipient.

The term "autograft" as utilized herein refers to tissue that is extracted from the intended recipient of the implant.

The term "biodegradable" includes that all or parts of the matrix will degrade over time by the action of enzymes, by hydrolytic action and/or by other similar mechanisms in the human body. In various embodiments, "biodegradable" includes that a matrix (e.g., sponge, sheet, etc.) can break down or degrade within the body to non-toxic components after or while a therapeutic agent has been or is being released. By "bioerodible" it is meant that the matrix will erode or degrade over time due, at least in part, to contact with substances found in the surrounding tissue, fluids or by cellular action. By "bioabsorbable" or "bioresorbable" it is meant that the matrix will be broken down and absorbed within the human body, for example, by a cell or tissue. "Biocompatible" means that the matrix will not cause substantial tissue irritation or necrosis at the target tissue site.

The term "compression" refers to a reduction in size or an increase in density when a force is applied to the matrix.

The term "mammal" refers to organisms from the taxonomy class "mammalian," including but not limited to humans, other primates such as chimpanzees, apes, orangutans and monkeys, rats, mice, cats, dogs, cows, horses, etc.

The term "resorbable" includes biologic elimination of the products of degradation by metabolism and/or excretion over time, for example, usually months.

The term "particle" refers to pieces of a substance of all shapes, sizes, thickness and configuration such as fibers, threads, narrow strips, thin sheets, clips, shards, etc., that posses regular, irregular or random geometries. In some embodiments, the particles are regular, e.g., spherical or irregular. It should be understood that some variation in dimension will occur in the production of the particles and particles demonstrating such variability in dimensions are within the scope of the present application.

The term "target tissue site" is intended to mean the location of the tissue to be treated. Typically the placement site of the matrix will be the same as the target site to provide for optimal targeted drug delivery or bone regeneration. However, the present application also contemplates positioning the matrix at a placement site at or near the target site such that the therapeutic agent (e.g., growth factor) can be delivered to the surrounding vasculature, which carries the agent to the desired nearby target site. As used herein, the term "at or near" includes embodiments where the placement site and target site are within close proximity (e.g., within about 1 mm to 5 cm).

A "therapeutically effective amount" or "effective amount" is such that when administered, the drug (e.g., growth factor) results in alteration of the biological activity, such as, for example, promotion of bone, cartilage and/or other tissue (e.g., vascular tissue) growth, inhibition of inflammation, reduction or alleviation of pain, improvement in the condition through inhibition of an immunologic response, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the implantable matrix is designed not only for administration of the stem cells, but also for sustained release of a therapeutic agent such as a growth factor. Thus, in some embodiments, the implantable matrix comprises an effective amount of a growth factor for sustained release for a desired profile of a therapeutic agent.

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug. Thus, in some embodiments, the implantable matrix comprises an effective amount of a growth factor for immediate release of a desired amount of a therapeutic agent.

The phrases "prolonged release", "sustained release" or "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the matrix and/or component thereof, or as the result of metabolic transformation or dissolution of the therapeutic agent(s) or conjugates of therapeutic agent(s). The release need not be linear and can be pulse type dosing.

The "matrix" of the present application is utilized as a scaffold for bone and/or cartilage repair, regeneration, and/or augmentation. Typically, the matrix provides a 3-D structure of interconnecting pores, which acts as a pliant scaffold for cell migration. The morphology of the matrix guides cell migration and cells are able to migrate into or over the matrix. The cells then are able to proliferate and synthesize new tissue and form bone and/or cartilage. In some embodiments, the matrix is resorbable.

In some embodiments, the matrix can be shaped. The term "shaped" includes that the matrix including any particles that may be present is formed into sheets, plates, disks, cones, pins, screws, tubes, teeth, bones, portion of bone, wedges, cylinders, threaded cylinders, and the like, as well as more complex geometric configurations.

The terms "treating" and "treatment" when used in connection with a disease or condition refer to executing a protocol that may include a repair procedure (e.g., osteochondral repair procedure), administering one or more matrices to a patient (human or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, do not require a cure, and specifically include protocols that have only a marginal effect on the patient. In some embodiments, the implantable matrix can be used to treat subchondral, osteochondral, hyaline cartilage and/or condyle defects.

The matrix may be osteogenic. The term "osteogenic" as used herein includes the ability of the matrix to enhance or accelerate the growth of new bone tissue by one or more mechanisms such as osteogenesis, osteoconduction and or osteoinduction. In some embodiments, the matrix can be delivered to other surgical sites, particularly sites at which bone growth is desired. These include, for instance, the repair of the spine, (e.g., vertebrae fusion,) cranial defects, iliac crest back-filling, acetabular defects, in the repair of tibial plateau, long bone defects, spinal site defects or the like. Such methods can be used to treat major or minor defects in these or other bones caused by trauma (including open and closed fractures), disease, or congenital defects, for example.

The matrix may be osteoinductive. The term "osteoinductive" as used herein includes the ability of a substance to recruit cells from the host that have the potential for forming new bone and repairing bone tissue. Most osteoinductive materials can stimulate the formation of ectopic bone in soft tissue.

The matrix may be osteoconductive. The term "osteoconductive" as utilized herein includes the ability of a non-osteoinductive substance to serve as a suitable template or substrate along which bone may grow.

The matrix may be implantable. The term "implantable" as utilized herein refers to a biocompatible device retaining potential for successful placement within a mammal. The expression "implantable device" and expressions of like import as utilized herein refer to any object implantable through surgery, injection, or other suitable means whose primary function is achieved either through its physical presence or mechanical properties.

The term "carrier" includes a diluent, adjuvant, buffer, excipient, or vehicle with which a composition can be administered. Carriers can include sterile liquids, such as, for example, water and oils, including oils of petroleum, animal, vegetable or synthetic origin, such as, for example, peanut oil, soybean oil, mineral oil, sesame oil, or the like. The growth factor may include a carrier.

The term "excipient" includes a non-therapeutic agent added to a pharmaceutical composition to provide a desired consistency or stabilizing effect. Excipients for parenteral formulations, include, for example, oils (e.g., canola, cottonseed, peanut, safflower, sesame, soybean), fatty acids and salts and esters thereof (e.g., oleic acid, stearic acid, palmitic acid), alcohols (e.g., ethanol, benzyl alcohol), polyalcohols (e.g., glycerol, propylene glycols and polyethylene glycols, e.g., PEG 3350), polysorbates (e.g., polysorbate 20, polysorbate 80), gelatin, albumin (e.g., human serum albumin), salts (e.g., sodium chloride), succinic acid and salts thereof (e.g., sodium succinate), amino acids and salts thereof (e.g., alanine, histidine, glycine, arginine, lysine), acetic acid or a salt or ester thereof (e.g., sodium acetate, ammonium acetate), citric acid and salts thereof (e.g., sodium citrate), benzoic acid and salts thereof, phosphoric acid and salts thereof (e.g., monobasic sodium phosphate, dibasic sodium phosphate), lactic acid and salts thereof, polylactic acid, glutamic acid and salts thereof (e.g., sodium glutamate), calcium and salts thereof (e.g., $CaCl_2$, calcium acetate), phenol, sugars (e.g., glucose, sucrose, lactose, maltose, trehalose), erythritol, arabitol, isomalt, lactitol, maltitol, mannitol, sorbitol, xylitol, nonionic surfactants (e.g., TWEEN 20, TWEEN 80), ionic surfactants (e.g., sodium dodecyl sulfate), chlorobutanol, DMSO, sodium hydroxide, glycerin, m-cresol, imidazole, protamine, zinc and salts thereof (e.g., zinc sulfate), thimerosal, methylparaben, propylparaben, carboxymethylcellulose, chlorobutanol, or heparin. The growth factor, if present, may include an excipient.

The term "lyophilized" or "freeze-dried" includes a state of a substance that has been subjected to a drying procedure such as lyophilization, where at least 50% of moisture has been removed. The matrix may be lyophilized or freeze-dried.

A "preservative" includes a bacteriostatic, bacteriocidal, fungistatic or fungicidal compound that is generally added to formulations to retard or eliminate growth of bacteria or other contaminating microorganisms in the formulations. Preservatives include, for example, benzyl alcohol, phenol, benzalkonium chloride, m-cresol, thimerosol, chlorobutanol, methylparaben, propylparaben and the like. Other examples of pharmaceutically acceptable preservatives can be found in the USP. The growth factor and/or matrix may have preservatives or be preservative free.

Reference will now be made in detail to certain embodiments of the invention. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

In some embodiments, an implantable matrix is provided that is configured to fit at or near a target tissue site, the matrix comprising: stem cells and calcium and/or phosphate ions. The matrix may be formed from a biodegradable polymer and in some embodiments, a plurality of particles embedded within the polymer. The ceramic particles may be embedded in the polymer uniformly or randomly. The particles may offer the advantage of reducing compression. The matrix is configured to allow influx of at least one of progenitor, bone and/or cartilage cells therein.

The matrix is considered to comprise the calcium and/or phosphate ions and the stem cells if the calcium and/or phosphate ions and stem cells are embedded in the matrix, rest on the surface of the matrix, or are suspended in the hydration fluid within the matrix.

The headings below are not meant to limit the disclosure in any way; embodiments under any one heading may be used in conjunction with embodiments under any other heading.

Calcium and/or Phosphate Ions

Calcium and/or phosphate ions act as a signal to stem cells. As bone is resorbed by osteoclasts, calcium and/or phosphate ions instruct nearby progenitor stem cells to become osteoblasts and to form osteoids, which ultimately deposit new bone. The phrase "calcium and/or phosphate ions" means the presence of exclusively calcium ions, exclusively phosphate ions, or a combination calcium and phosphate ions, e.g., a ratio of calcium to phosphate of between 1:20 and 1:10 or between 1:10 and 1:5 or between 1:5 and 1:3 or between 1:3 and 1:2 or between 1:2: 1 and 1:1 or between 1:1 and 2:1 or between 2:1 and 3:1 or between 3:1 and 5:1 or between 5:1 and 10:1 or between 10:1 and 20:1.

The calcium and/or phosphate ions are micron in size (e.g., 0.01-10 microns or 0.1 to 1 microns) and may, for example, be in the form of individual ions, or complexed as calcium phosphate ions of tricalcium phosphate, hydroxyapatite or combinations thereof. In some embodiments, the calcium and/or phosphate ions that are present are present in an amount of up to 100 times the number of stem cells that are being utilized. For example, the number of ions may be 1-100 times the number of stem cells or 2-50 times the number of stem cells or 5-25 times the number of stem cells or 5-15 times the number of stem cells or 5-10 times the number of stem cells or 10-15 times the number of stem cells.

In some embodiments, the ions are made synthetically, or they are derived from bone or they are obtained from a combination of these sources.

In some embodiments, the ions are in a solution that is used to hydrate and to deliver the stem cells to the matrix. In other embodiments, they may be added to a collagen slurry during the manufacture of the matrix.

Although not wishing to be bound by any one theory of interaction, it is believed that the ions set up an environment that is conducive for new bone deposition under the conditions of the local pH, and the high concentration of calcium phosphate ions signals the osteoblast cells to begin to lay day osteoid (unimineralized precursor tissue to bone) and can use the readily available smaller calcium phosphate ions as raw materialize to "mineralize" the osteoid.

In addition, the calcium phosphate ions may act as nidus for the bone formation by providing a surface for osteoblasts to anchor, which is needed to facilitate bone formation. For example, it is known that if one places large ceramic particles (e.g., about 5 mm in diameter) in a soft tissue site and waits a very long time (months) it will eventually form small amounts of bone on the ceramic particle surfaces. This time period may be due to the time that is takes for the macrophages to release some calcium phosphate ions from the very large ceramic particles surfaces and for stem cells to migrate into the area. Under some embodiments of the methods of the present invention, the bone formation process may be accelerated by providing the both the calcium and/or phosphate ions with the stem cells.

Stem Cells

Stem cells have the potential to differentiate into any type of cell. The stem cells of the present invention may, for example, be mesenchymal stem cells, such as human mesenchymal stem cells. These stem cells may be autologous, allogenic or from xenogenic sources, and can be from bone marrow donors, tissue biopsies, allograft bone donors, embryonic sources, or post-natal sources.

As persons of ordinary skill in the art are aware, these cells may, for example, be derived from the bone marrow of the iliac crest, femora tibiae, spine, rib or other medulary spaces. They may also, for example, be derived from tissue biopsies containing stem cells, allograft bone donors, the embryonic yolk sac, placenta, umbilical cord, periosteum, fetal and adolescent skin and blood.

The amount of stem cells that are administered will preferably be an effective dose. In some embodiments, this may be between about $10^3$ and $10^6$ stem cells per milliliter of composition, or between about $10^3$ and $10^4$ stem cells per milliliter of composition or between about $10^4$ and $10^5$ stem cells per milliliter of composition or between about $10^5$ and $10^6$ stem cells per milliliter of composition.

The stem cells can be used to seed the matrix, either on the interior or on the exterior of the matrix. Thus, by way of a non-limiting example, the cells may be transferred to a matrix that is uncoated or coated with for example collagen, gelatin, fibronectin, ornithine, vitronectin or extracellular membrane protein. Further, the stem cells may be cultured in for example, a medium that comprises serum.

Matrix

The matrix provides a tissue scaffold for the cells to guide the process of tissue formation in vivo in three dimensions, and may, for example, be formed from collagen and/or ceramic material. The ceramic material may, for example, be porous and in particulate form, or in the form of an implant. The morphology of the matrix guides cell migration and cells are able to migrate into or over the matrix. The matrix also provides a framework around which the stem cells may grow. The cells then are able to proliferate and synthesize new tissue and to form bone and/or cartilage. In some embodiments, one or more tissue matrices are stacked on one another.

In some embodiments, the matrix has a fluid "soak load" of 50-100% of its volume and is loaded with 0.5-30 million cells per cc (e.g., 5-10 million per cc). The volume of matrix used is dependent on the size of the bone defect being filled.

The matrix may further comprise DBM (demineralized bone matrix) or DBM particles or a growth factor such a BMP.

In some embodiments, the growth factor (e.g., rhBMP-2) will be more evenly distributed throughout the interior of the matrix and facilitate more uniform bone growth throughout the whole matrix. In some embodiments, the growth factor (e.g., rhBMP-2) is temporarily retained within the matrix so as to limit new bone formation to within the matrix.

In some embodiments, the matrix comprises a plurality of pores and thus is porous. The term "porous" means that the matrix has a plurality of pores. These pores are a size large enough to allow influx of blood, other bodily fluid, and progenitor and/or bone and/or cartilage cells into the interior to guide the process of tissue formation in vivo in three dimensions.

In some embodiments, at least 10% of the pores are between about 50 micrometers and about 500 micrometers at their widest points. In some embodiments, at least 20% of the pores are between about 50 micrometers and about 250 micrometers at their widest points. In some embodiments, at least 30% of the pores are between about 50 micrometers and about 150 micrometers at their widest points. In some embodiments, at least 50% of the pores are between about 10 micrometers and about 500 micrometers at their widest points. In some embodiments, at least 90% of the pores are between about 50 micrometers and about 250 micrometers at their widest points. In some embodiments, at least 95% of the pores are between about 50 micrometers and about 150 micrometers at their widest points. In some embodiments, 100% of the pores are between about 10 micrometers and about 500 micrometers at their widest points.

In some embodiments, the matrix has a porosity of at least about 30%, at least about 50%, at least about 60%, at least about 70%, at least about 90%, at least about 95%, or at least about 99%. Within these pores, the matrix may support ingrowth of cells, and/or formation or remodeling of bone, cartilage and/or vascular tissue.

In some embodiments, when a growth factor is present, the porous interior can hold the growth factor within the matrix and because the interior is porous, the growth factor can be evenly distributed throughout the matrix when growth factor is injected into the matrix. In some embodiments, the growth factor will be held within the interior of the matrix and released into the environment surrounding the matrix (e.g., bone defect, osteochondral defect, etc.) as the matrix degrades over time.

In some embodiments, the matrix comprises biodegradable polymeric and non-polymeric material. For example, the matrix may comprise one or more poly (alpha-hydroxy acids), poly (lactide-co-glycolide) (PLGA), polylactide (PLA), poly(L-lactide), polyglycolide (PG), polyethylene glycol (PEG) conjugates of poly (alpha-hydroxy acids), polyorthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, POE, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, silicone, hyaluronic acid, chitosan, or combinations thereof.

In some embodiments, the matrix (e.g., exterior and/or interior) comprises collagen. Exemplary collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof.

In some embodiments, the matrix comprises collagen-containing biomaterials from the implant market which, when placed in a bone defect, provide scaffolding around which the patient's new bone and/or cartilage will grow, gradually replacing the carrier matrix as the target site heals. Examples of suitable carrier matrices may include, but are not limited to, the MasterGraft® Matrix produced by Medtronic Sofamor Danek, Inc., Memphis, Tenn.; MasterGraft® Putty produced by Medtronic Sofamor Danek, Inc., Memphis, Tenn.; Absorbable Collagen Sponge ("ACS") produced by Integra LifeSciences Corporation, Plainsboro, N.J.; bovine skin collagen fibers coated with hydroxyapatite, e.g. Healos® marketed by Johnson & Johnson, USA; collagen sponges, e.g. Hemostagene® marketed by Coletica S A, France, or e.g. Helisat® marketed by Integra Life Sciences Inc., USA; and Collagraft® Bone Graft Matrix produced by Zimmer Holdings, Inc., Warsaw, Ind.

Other extracellular components may be part of the matrix, and may facilitate osteoconduction or osteoinduction. By varying the ratios of these components, the surgical handling properties of the cell-biomatrix implants can be adjusted in a range from a dimensionally stable matrix, such as a sponge or film to a powder.

In some embodiments, the matrix has a thickness of from 1 mm to 15 mm, or from about 2 mm to about 10 mm, or 3 mm to about 5 mm. Different bone defects (e.g., osteochondral defects) may require different matrices thicknesses.

In some embodiments, the matrix has a density of between about 1.6 g/cm$^3$, and about 0.05 g/cm$^3$. In some embodiments, the matrix has a density of between about 1.1 g/cm$^3$, and about 0.07 g/cm$^3$. For example, the density may be less than about 1 g/cm$^3$, less than about 0.7 g/cm$^3$, less than about 0.6 g/cm$^3$, less than about 0.5 g/cm$^3$, less than about 0.4 g/cm$^3$, less than about 0.3 g/cm$^3$, less than about 0.2 g/cm$^3$, or less than about 0.1 g/cm$^3$.

The shape of the matrix may be tailored to the site at which it is to be situated. For example, it may be in the shape of a morsel, a plug, a pin, a peg, a cylinder, a block, a wedge, a sheet, a strip, etc. The term "shape" refers to a determined or regular form or configuration in contrast to an indeterminate or vague form or configuration (as in the case of a lump or other solid mass of no special form) and is characteristic of such materials as sheets, plates, disks, cores, tubes, wedges, cylinders, or the like. This includes forms ranging from regular, geometric shapes to irregular, angled, or non-geometric shapes, or combinations of features having any of these characteristics.

In some embodiments, the diameter or diagonal of the matrix can range from 1 mm to 50 mm. In some embodiments, the diameter or diagonal of the matrix can range from 1 mm to 30 mm, or 5 mm to 10 mm, which is small enough to fit through an endoscopic cannula, but large enough to minimize the number of matrices needed to fill a large the bone defect (e.g., an osteochondral defect).

Ceramic Particles

In some embodiments, the matrix is compression resistant. Thus, it may resist reduction in size or an increase in density when a force is applied as compared to matrices without the particles disposed therein. In various embodiments, the matrix resists compression by at 10%, 15%, 20%, 25%, 30%, 35%, 40%, 45%, 50%, 55% or more in one or all directions when a force is applied to the matrix.

Compression resistance is needed for many tissue engineering applications such as tibial plateau fractures, acetabular defects, long bone comminuted fractures, oral maxillofacial defects, spinal fusions, and cartilage subchondral defects. Compression resistant matrices will help facilitate adequate volumes of newly formed bone.

In some embodiments, the ceramic particles comprise at least 10%, 15%, 20%, 25%, 30%, 35%, 40%, 45%, 50%, 55%, 60%, 65%, 70%, 75%, 80%, 85%, 90%, 95% by weight of the matrix.

In some embodiments, the ceramic particles comprise cortical, cancellous, and/or corticocancellous, allogenic, xenogenic or transgenic bone tissue. The bone component can be fully mineralized or partially or fully demineralized or combinations thereof. The bone component can consist of fully mineralized or partially or fully demineralized bone.

In some embodiments, the ceramic particles are not aggregated (e.g., they do not clump together in a mass) in the matrix.

In some embodiments, the ceramic particles are randomly distributed throughout the matrix. In other embodiments, the ceramic particles are uniformly or evenly distributed throughout the matrix. In some embodiments, the ceramic particles may be dispersed in the matrix using a dispersing agent. In other embodiments, the ceramic particles may be stirred in the polymer and the mechanical agitation will distribute the particles in the matrix until the desired distribution is reached (e.g., random or uniform).

In some embodiments, the matrix may comprise a resorbable ceramic (e.g., hydroxyapatite, tricalcium phosphate, bioglasses, calcium sulfate, etc.) tyrosine-derived polycarbonate poly (DTE-co-DT carbonate), in which the pendant group via the tyrosine—an amino acid—is either an ethyl ester (DTE) or free carboxylate (DT) or combinations thereof.

In some embodiments, the matrix and the ceramic particles comprise a resorbable ceramic, bone, hyaluronic acid, chitosan or combinations thereof.

In some embodiments, the matrix may contain an inorganic material, such as an inorganic ceramic and/or bone substitute material. Exemplary inorganic materials or bone substitute materials include but are not limited to aragonite, dahlite, calcite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™, fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, by including inorganic ceramics, such as for example, calcium phosphate, in the matrix, this will facilitate the prevention of local bone resorption by providing slower release of the growth factor due to its increased binding potential and also act as a local source of calcium and phosphate to the cells attempting to deposit new bone.

In some embodiments, the ceramic particles in the matrix comprise tricalcium phosphate and hydroxyapatite in a ratio of about 80:20 to about 90:10. In some embodiments, the ceramic particles in the matrix comprise tricalcium phosphate and hydroxyapatite in a ratio of about 85:15.

In some embodiments, the ceramic particles may be formed from silicon materials.

Examples of ceramic materials are described in US 2009/0149569A1 to Shastri, the disclosure of which is incorporated by references as if set for the fully herein.

Method of Making the Matrix

In some embodiments, the matrix may be made by injection molding, compression molding, blow molding, thermoforming, die pressing, slip casting, electrochemical machining, laser cutting, water-jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

One form of manufacturing the matrix involves casting the matrix material in a mold. The matrix material can take on the shape of the mold such as, crescent, quadrilateral, rectangular, cylindrical, plug, or any other shape. Additionally, the surface of the mold may be smooth or may include raised features or indentations to impart features to the matrix. Features from the mold can be imparted to the matrix as the matrix material in the mold is dried. In particular aspects, a roughened or friction engaging surface can be formed on the superior surface and/or the inferior surface of the matrix body. In some embodiments, protuberances or raised portions can be imparted on the superior surface and/or the inferior surface from the mold. Such examples of protuberances or raised portions are ridges, serrations, pyramids, and teeth, or the like.

In some embodiments, in manufacturing the matrix, a mixture of the matrix material (e.g., collagen) is combined with the particles and a liquid to wet the material and form a slurry. Any suitable liquid can be used including, for example, aqueous preparations such as water, saline solution (e.g. physiological saline), sugar solutions, protic organic solvents, or liquid polyhydroxy compounds such as glycerol and glycerol esters, or mixtures thereof. The liquid may, for example, constitute about 5 to about 70 weight percent of the mixed composition prior to the molding operation. Certain liquids such as water can be removed in part or essentially completely from the formed matrix using conventional drying techniques such as air drying, heated drying, lyophilization, or the like.

In one embodiment of manufacture, a collagen mixture can be combined with particles and a liquid, desirably with an aqueous preparation, to form a slurry. Excess liquid can be removed from the slurry by any suitable means, including for example by applying the slurry to a liquid-permeable mold or form and draining away excess liquid.

Before, during or after molding, including in some instances the application of compressive force to the collagen containing material, the collagen material can be subjected to one or more additional operations such as heating, lyophilizing and/or crosslinking to make the porous collagen interior or exterior of the matrix the desired porosity. In this regard, crosslinking can be used to improve the strength of the formed matrix. Alternatively, one or more of the surface of the matrix can be crosslinked to reduce the size of the pores of the porous interior and thereby form the exterior of the matrix that is less permeable and/or less porous than the porous interior. Crosslinking can be achieved, for example, by chemical reaction, the application of energy such as radiant energy (e.g. UV light or microwave energy), drying and/or heating and dye-mediated photo-oxidation; dehydrothermal treatment; enzymatic treatment or others.

Chemical crosslinking agents will generally be preferred, including those that contain bifunctional or multifunctional reactive groups, and that react with the matrix. Chemical crosslinking can be introduced by exposing the matrix material to a chemical crosslinking agent, either by contacting it with a solution of the chemical crosslinking agent or by exposure to the vapors of the chemical crosslinking agent. This contacting or exposure can occur before, during or after a molding operation. In any event, the resulting material can then be washed to remove substantially all remaining amounts of the chemical crosslinker if needed or desired for the performance or acceptability of the final implantable matrix.

Suitable chemical crosslinking agents include mono- and dialdehydes, including glutaraldehyde and formaldehyde; polyepoxy compounds such as glycerol polyglycidyl ethers, polyethylene glycol diglycidyl ethers and other polyepoxy and diepoxy glycidyl ethers; tanning agents including polyvalent metallic oxides such as titanium dioxide, chromium dioxide, aluminum dioxide, zirconium salt, as well as organic tannins and other phenolic oxides derived from plants; chemicals for esterification or carboxyl groups followed by reaction with hydrazide to form activated acyl azide functionalities in the collagen; dicyclohexyl carbodiimide and its derivatives as well as other heterobifunctional crosslinking agents; hexamethylene diisocyante; and/or sugars, including glucose, will also crosslink the matrix material.

In some embodiments, the matrices are formed by mixing the particles in with a polymer slurry such as collagen and pouring it into a shaped mold. The composite mixture is freeze dried and possibly chemically crosslinked and cut to the final desired shape.

In some embodiments, the matrix may comprise sterile and/or preservative free material. The matrix can be implanted by hand or machine in procedures such as for example, laparoscopic, arthroscopic, neuroendoscopic, endoscopic, rectoscopic procedures or the like.

As noted above in order to incorporate the stems cells, they may be hydrated, if necessary, and delivered into the matrix that contains the calcium and/or phosphate ions.

Growth Factors

In some embodiments, a growth factor and/or therapeutic agent may be disposed on or in the matrix by hand, electrospraying, ionization spraying or impregnating, vibratory dispersion (including sonication), nozzle spraying, compressed-air-assisted spraying, injecting, brushing and/or pouring. For example, a growth factor such as rhBMP-2 may be disposed on or in a biodegradable matrix by the surgeon before the biodegradable matrix is administered or the matrix may be pre-loaded with the growth factor by the manufacturer beforehand.

These growth factors include but are not limited to osteoinductive agents (e.g., agents that cause new bone growth in an area where there was none) and/or osteoconductive agents (e.g., agents that cause ingrowth of cells into and/or through the matrix). Osteoinductive agents can be polypeptides or polynucleotides compositions. Polynucleotide compositions of the osteoinductive agents include, but are not limited to, isolated Bone Morphogenic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta) polynucleotides. Polynucleotide compositions of the osteoinductive agents include, but are not limited to, gene therapy vectors harboring polynucleotides encoding the osteoinductive polypeptide of interest. Gene therapy methods often utilize a polynucleotide, which codes for the osteoinductive polypeptide operatively linked or associated to a promoter or any other genetic elements necessary for the expression of the osteoinductive polypeptide by the target tissue. Such gene therapy and delivery techniques are known in the art (see, for example, International Publication No. WO90/11092, the disclosure of which is herein incorporated by reference in its entirety). Suitable gene therapy vectors include, but are not limited to, gene therapy vectors that do not integrate into the host genome. Alternatively, suitable gene therapy vectors include, but are not limited to, gene therapy vectors that integrate into the host genome.

In some embodiments, the polynucleotide is delivered in plasmid formulations. Plasmid DNA or RNA formulations refer to polynucleotide sequences encoding osteoinductive polypeptides that are free from any delivery vehicle that acts to assist, promote or facilitate entry into the cell, including viral sequences, viral particles, liposome formulations, lipofectin, precipitating agents or the like. Optionally, gene therapy compositions can be delivered in liposome formulations and lipofectin formulations, which can be prepared by methods well known to those skilled in the art. General methods are described, for example, in U.S. Pat. Nos. 5,593,972, 5,589,466, and 5,580,859, the disclosures of which are herein incorporated by reference in their entireties.

Gene therapy vectors further comprise suitable adenoviral vectors including, but not limited to for example, those described in U.S. Pat. No. 5,652,224, which is herein incorporated by reference.

Polypeptide compositions of the isolated osteoinductive agents include, but are not limited to, isolated Bone Morphogenic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta707) polypeptides. Polypeptide compositions of the osteoinductive agents include, but are not limited to, full length proteins, fragments or variants thereof.

Variants of the isolated osteoinductive agents include, but are not limited to, polypeptide variants that are designed to increase the duration of activity of the osteoinductive agent in vivo.

Typically, variant osteoinductive agents include, but are not limited to, full length proteins or fragments thereof that are conjugated to polyethylene glycol (PEG) moieties to increase their half-life in vivo (also known as pegylation). Methods of pegylating polypeptides are well known in the art (See, e.g., U.S. Pat. No. 6,552,170 and European Pat. No. 0,401,384 as examples of methods of generating pegylated polypeptides). In some embodiments, the isolated osteoinductive agent(s) are provided as fusion proteins. In one embodiment, the osteoinductive agent(s) are available as fusion proteins with the Fc portion of human IgG. In another embodiment, the osteoinductive agent(s) are available as hetero- or homodimers or multimers. Examples of some fusion proteins include, but are not limited to, ligand fusions between mature osteoinductive polypeptides and the Fc portion of human Immunoglobulin G (IgG). Methods of making fusion proteins and constructs encoding the same are well known in the art.

Isolated osteoinductive agents that are included within a matrix are typically sterile. In a non-limiting method, sterility is readily accomplished for example by filtration through sterile filtration membranes (e.g., 0.2 micron membranes or filters). In one embodiment, the matrix includes osteoinductive agents comprising one or more members of the family of Bone Morphogenic Proteins ("BMPs"). BMPs are a class of proteins thought to have osteoinductive or growth-promoting activities on endogenous bone tissue, or function as procollagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, isolated osteoinductive agents that are loaded in the matrix include osteoclastogenesis inhibitors to inhibit bone resorption of the bone tissue surrounding the site of implantation by osteoclasts. Osteoclast and osteoclastogenesis inhibitors include, but are not limited to, osteoprotegerin polynucleotides or polypeptides, as well as mature osteoprotegerin proteins, polypeptides or polynucleotides encoding the same. Osteoprotegerin is a member of the TNF-receptor superfamily and is an osteoblast-secreted decoy receptor that functions as a negative regulator of bone resorption. This protein specifically binds to its ligand, osteoprotegerin ligand (TNFSF11/OPGL), both of which are key extracellular regulators of osteoclast development.

Osteoclastogenesis inhibitors that can be loaded in the matrix further include, but are not limited to, chemical compounds such as bisphosphonate, 5-lipoxygenase inhibitors such as those described in U.S. Pat. Nos. 5,534,524 and 6,455,541 (the contents of which are herein incorporated by reference in their entireties), heterocyclic compounds such as those described in U.S. Pat. No. 5,658,935 (herein incorporated by reference in its entirety), 2,4-dioxoimidazolidine and imidazolidine derivative compounds such as those described in U.S. Pat. Nos. 5,397,796 and 5,554,594 (the contents of which are herein incorporated by reference in their entireties), sulfonamide derivatives such as those described in U.S. Pat. No. 6,313,119 (herein incorporated by reference in its entirety), or acylguanidine compounds such as those described in U.S. Pat. No. 6,492,356 (herein incorporated by reference in its entirety).

In another embodiment, isolated osteoinductive agents that can be loaded in the matrix include one or more members of the family of Connective Tissue Growth Factors ("CTGFs"). CTGFs are a class of proteins thought to have growth-promoting activities on connective tissues. Known members of the CTGF family include, but are not limited to, CTGF-1, CTGF-2, CTGF-4 polynucleotides or polypeptides thereof, as well as mature proteins, polypeptides or polynucleotides encoding the same.

In another embodiment, isolated osteoinductive agents that can be loaded in the matrix include one or more members of the family of Vascular Endothelial Growth Factors ("VEGFs"). VEGFs are a class of proteins thought to have growth-promoting activities on vascular tissues. Known members of the VEGF family include, but are not limited to, VEGF-A, VEGF-B, VEGF-C, VEGF-D, VEGF-E or polynucleotides or polypeptides thereof, as well as mature VEGF-A, proteins, polypeptides or polynucleotides encoding the same.

In another embodiment, isolated osteoinductive agents that can be loaded in the matrix include one or more members of the family of Transforming Growth Factor-beta ("TGFbetas"). TGF-betas are a class of proteins thought to have growth-promoting activities on a range of tissues, including connective tissues. Known members of the TGF-beta family include, but are not limited to, TGF-beta-1, TGF-beta-2, TGF-beta-3, polynucleotides or polypeptides thereof, as well as mature protein, polypeptides or polynucleotides encoding the same.

In another embodiment, isolated osteoinductive agents that can be loaded in the matrix include one or more Growth Differentiation Factors ("GDFs"). Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same; GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same; GDF-3 polynucleotides or polypeptides corresponding to GenBank Accession Numbers AF263538, BC030959, AAF91389, AAQ89234, or Q9NR23, as well as mature GDF-3 polypeptides or polynucleotides encoding the same; GDF-7 polynucleotides or polypeptides corresponding to GenBank Accession Numbers AB158468, AF522369, AAP97720, or Q7Z4P5, as well as mature GDF-7 polypeptides or polynucleotides encoding the same; GDF-10 polynucleotides or polypeptides corresponding to GenBank Accession Numbers BCO28237 or AAH28237, as well as mature GDF-10 polypeptides or polynucleotides encoding the same; GDF-11 polynucleotides or polypeptides corresponding to GenBank Accession Numbers AF100907, NP_005802 or 095390, as well as mature GDF-11 polypeptides or polynucleotides encoding the same; and GDF-15 polynucleotides or polypeptides corresponding to GenBank Accession Numbers BC008962, BC000529, AAH00529, or NP_004855, as well as mature GDF-15 polypeptides or polynucleotides encoding the same.

In another embodiment, isolated osteoinductive agents that can be loaded in the matrix include Cartilage Derived Morphogenic Protein (CDMP) and Lim Mineralization Protein (LMP) polynucleotides or polypeptides. Known CDMPs and LMPs include, but are not limited to, CDMP-1, CDMP-2, LMP-1, LMP-2, or LMP-3.

CDMPs and LMPs useful as isolated osteoinductive agents that can be loaded in the matrix include, but are not limited to, the following CDMPs and LMPs: CDMP-1 polynucleotides and polypeptides corresponding to GenBank Accession Numbers NM_000557, U13660, NP_000548 or P43026, as well as mature CDMP-1 polypeptides or polynucleotides encoding the same; CDMP-2 polypeptides corresponding to GenBank Accession Numbers or P55106, as well as mature CDMP-2 polypeptides; LMP-1 polynucleotides or polypeptides corresponding to GenBank Accession Numbers AF345904 or AAK30567, as well as mature LMP-1 polypeptides or polynucleotides encoding the same; LMP-2 polynucleotides or polypeptides corresponding to GenBank Accession Numbers AF345905 or AAK30568, as well as mature LMP-2 polypeptides or polynucleotides encoding the same; and LMP-3 polynucleotides or polypeptides corresponding to GenBank Accession Numbers AF345906 or AAK30569, as well as mature LMP-3 polypeptides or polynucleotides encoding the same.

In another embodiment, isolated osteoinductive agents that can be loaded in the matrix include one or more members of any one of the families of Bone Morphogenic Proteins (BMPs), Connective Tissue Growth Factors (CTGFs), Vascular Endothelial Growth Factors (VEGFs), Osteoprotegerin or any of the other osteoclastogenesis inhibitors, Growth Differentiation Factors (GDFs), Cartilage Derived Morphogenic Proteins (CDMPs), Lim Mineralization Proteins (LMPs), or Transforming Growth Factor-betas (TGF-betas), as well as mixtures or combinations thereof.

In another embodiment, the one or more isolated osteoinductive agents that can be loaded in the matrix are selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, or any combination thereof; CTGF-1, CTGF-2, CGTF-3, CTGF-4, or any combination thereof; VEGF-A, VEGF-B, VEGF-C, VEGF-D, VEGF-E, or any combination thereof; GDF-1, GDF-2, GDF-3, GDF-7, GDF-10, GDF-11, GDF-15, or any combination thereof; CDMP-1, CDMP-2, LMP-1, LMP-2, LMP-3, and/or any combination thereof; Osteoprotegerin; TGF-beta-1, TGF-beta-2, TGF-beta-3, or any combination thereof; or any combination of one or more members of these groups.

In some embodiments, BMP-2, BMP-7 and/or GDF-5 may be used at 1-2 mg/cc of matrix. The concentrations of growth factor can be varied based on the desired length or degree of osteogenic effects desired. Similarly, one of skill in the art will understand that the duration of sustained release of the growth factor can be modified by the manipulation of the compositions of the matrix, such as for example, microencapsulation of the growth factor within polymers. The sustained release matrix can therefore be designed to provide customized time release of growth factors that stimulate the natural healing process.

The growth factor may contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. In some embodiments, the growth factor may comprise sterile and/or preservative free material.

These above inactive ingredients may have multi-functional purposes including the carrying, stabilizing and controlling the release of the growth factor and/or other therapeutic agent(s). The sustained release process, for example, may be by a solution-diffusion mechanism or it may be governed by an erosion-sustained process.

In some embodiments, a pharmaceutically acceptable formulation comprising a growth factor is provided, wherein the formulation is a freeze-dried or lyophilized formulation. Typically, in the freeze-dried or lyophilized formulation an effective amount of a growth factor is provided. Lyophilized formulations can be reconstituted into solutions, suspensions, emulsions, or any other suitable form for administration or use. The lyophilized formulation may comprise the liquid used to reconstitute the growth factor. Lyophilized formulations are typically first prepared as liquids, then frozen and lyophilized. The total liquid volume before lyophilization can be less, equal to, or more than the final reconstituted volume of the lyophilized formulation. The lyophilization process is well known to those of ordinary skill in the art, and typically includes sublimation of water from a frozen formulation under controlled conditions.

Lyophilized formulations can be stored at a wide range of temperatures. Lyophilized formulations may be stored at or below 30° C., for example, refrigerated at 4° C., or at room temperature (e.g., approximately 25° C.).

Lyophilized formulations of the growth factor are typically reconstituted for use by addition of an aqueous solution to dissolve the lyophilized formulation. A wide variety of aqueous solutions can be used to reconstitute a lyophilized formulation. In some embodiments, lyophilized formulations can be reconstituted with a solution containing water (e.g., USP WFI, or water for injection) or bacteriostatic water (e.g., USP WFI with 0.9% benzyl alcohol). However, solutions comprising buffers and/or excipients and/or one or more pharmaceutically acceptable carries can also be used. In some embodiments, the solutions do not contain any preservatives (e.g., are preservative free).

Application of the Growth Factor to the Matrix

In some embodiments, a therapeutic agent (including one or more growth factors) may be disposed on or in the interior of the matrix by hand, electrospraying, ionization spraying or impregnating, vibratory dispersion (including sonication), nozzle spraying, compressed-air-assisted spraying, injecting, brushing and/or pouring.

Application of the growth factor to the matrix may occur at the time of surgery or by the manufacturer or in any other suitable manner. For example, the growth factor may be further reconstituted using a syringe and the syringe can be placed into the interior of the matrix via insertion of a needle or cannula (piercing the matrix) and placing it into the interior of the matrix and injecting the growth factor so it is evenly distributed throughout the porous interior.

In some embodiments, the growth factor may be applied to the matrix (e.g., collagen) prior to combining the materials and forming it into the final matrix shape. Indeed, the growth factor can be blended into the natural or synthetic polymer (i.e., POE) and poured into molds of the final shape of the matrix. Alternatively, the growth factor, such as a bone morphogenetic protein in a suitable liquid carrier, may be applied onto and/or into the porous loaded matrix after forming it into the final shape by soaking, dripping, injecting, spraying, etc.

In some embodiments, the interior of the matrix is loaded with BMP that functions as an osteoinductive factor. Indeed, the preferred osteoinductive factors are the recombinant human bone morphogenetic proteins (rhBMPs) because they are available in unlimited supply and do not transmit infectious diseases. In some embodiments, the bone morphogenetic protein is a rhBMP-2, rhBMP-4, rhBMP-7, or heterodimers thereof.

Recombinant BMP-2 can be used at a concentration of about 0.4 mg/ml to about 10.0 mg/ml, preferably near 1.5 mg/ml. However, any bone morphogenetic protein is contemplated including bone morphogenetic proteins designated as BMP-1 through BMP-18. BMPs are available from Wyeth, Cambridge, Mass. and the BMPs and genes encoding them may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

In some embodiments, the lyophilized growth factor (e.g., BMP) can be disposed in a vial by the manufacturer and then the surgeon can mix the diluent with the lyophilized growth factor. The matrix then can be parenterally administered to the target tissue site. The term "parenteral" as used herein refers to modes of administration that bypass the gastrointestinal tract, and include for example, intramuscular, intraperitoneal, intrasternal, subcutaneous, intra-operatively, intrathecally, intradiscally, peridiscally, epidurally, perispinally, intraarticular or combinations thereof.

The amount of growth factor, (e.g., bone morphogenic protein) may be sufficient to cause bone and/or cartilage growth. In some embodiments, the growth factor is rhBMP-2 and is contained in one or more matrices in an amount of from 1 to 2 mg per cubic centimeter of the biodegradable matrix. In some embodiments, the amount of rhBMP-2 morphogenic protein is from 2.0 to 2.5 mg per cubic centimeter (cc) of the biodegradable matrix.

In some embodiments, the growth factor is supplied in a liquid carrier (e.g., an aqueous buffered solution). Exemplary aqueous buffered solutions include, but are not limited to, TE, HEPES (2-[4-(2-hydroxyethyl)-1-piperazinyl]ethanesulfonic acid), MES (2-morpholinoethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM. In some embodiments, the BMP-2 is provided in a vehicle (including a buffer) containing sucrose, glycine, L-glutamic acid, sodium chloride, and/or polysorbate 80.

In some embodiments, upon implantation of the matrix or components that contact the matrix (e.g., plugs that are separate from the matrix on implantation), compression of the matrix is reduced or eliminated. As discussed above, if unwanted compression occurs, this causes the buffer from the bone growth factor to leak from the matrix, which causes higher concentrations of the growth factor (e.g., 2 mg to 2.5 mg of rhBMP-2 per cc of matrix) to remain on the matrix. This high concentration of growth factor may lead to local transient bone resorption and excess osteoclast formation and bone breakdown. This may result in poor integration of the matrix with surrounding host tissue and a failed repair. Thus, by employing a compression resistant matrix, unwanted leakage is reduced or avoided. In some embodiments, localized release of the growth factor may cause local irritation to the surrounding tissue. In some embodiments, the leaking of growth factor from the matrix may reduce a stable microenvironment for new bone and/or cartilage growth. It also may cause the matrix to fail to retain its full efficacy over time to maximally promote bone growth at a target site.

Additional Therapeutic Agents

The growth factors of the present application may be disposed on or in the matrix with other therapeutic agents. For example, the growth factor may be disposed on or in the carrier by electrospraying, ionization spraying or impregnating, vibratory dispersion (including sonication), nozzle spraying, compressed-air-assisted spraying, brushing and/or pouring.

Examples of therapeutic agents include but are not limited to IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dithiocarbamate, and other compounds, such as, for example, sulfasalazine.

Examples of therapeutic agents suitable for use also include, but are not limited to, an anti-inflammatory agent, analgesic agent, or osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin, and tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable analgesic agents include, but are not limited to, acetaminophen, bupivicaine, fluocinolone, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

In some embodiments, a statin may be used. Statins include, but are not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448, 784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

Kits

Various components and devices to administer the implantable matrix composition may be sterilizable. In various embodiments, one or more components of the matrix, and/or medical device to administer it may be sterilizable by radiation in a terminal sterilization step in the final packaging. Terminal sterilization of a product provides greater assurance of sterility than from processes such as an aseptic process, which require individual product components to be sterilized separately and the final package assembled in a sterile environment. However, any steps to sterilize components to be used in the processes of the present invention should be designed so as not to adversely affect the stem cells.

Typically, in various embodiments, gamma radiation is used in a sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In some embodiments, the implantable matrix may be packaged in a moisture resistant package and then terminally sterilized by gamma irradiation. In use, the surgeon removes the one or all components from the sterile package for use.

In various embodiments, electron beam (e-beam) radiation may be used to sterilize one or more components of the matrix. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the implantable matrix and/or one or more components of the matrix, including, but not limited to, gas sterilization, such as, for example, with ethylene oxide or steam sterilization.

In various embodiments, a kit is provided comprising the growth factor, matrix, stem cells, calcium and/or phosphate and/or diluents. The kit may include additional parts along with the implantable matrix combined together to be used to implant the matrix (e.g., wipes, needles, syringes, etc.). The kit may include the matrix in a first compartment, wherein the matrix comprises the stem cells and calcium and/or phosphate. The second compartment may include a vial holding a growth factor, diluent and any other instruments needed for the localized drug delivery. A third compartment may include gloves, drapes, wound dressings and other procedural supplies for maintaining sterility of the implanting process, as well as an instruction booklet, which may include a chart that shows how to implant the matrix after reconstituting the growth factor. A fourth compartment may include additional needles and/or sutures. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

Applications

The compositions and the methods of the present invention may, for example, be effective for repairing or regenerating bone defects in an animal or human who is in need of repair or regeneration. Thus, the matrix of the present application may be used to repair bone and/or cartilage at a target tissue site, e.g., one resulting from injury, defect brought about during the course of surgery, infection, malignancy or developmental malformation.

The matrix can be utilized in a wide variety of orthopedic, periodontal, neurosurgical, oral and maxillofacial surgical procedures such as the repair of simple and/or compound fractures and/or non-unions; external and/or internal fixations; joint reconstructions such as arthrodesis; general arthroplasty; cup arthroplasty of the hip; femoral and humeral head replacement; femoral head surface replacement and/or total joint replacement; repairs of the vertebral column including spinal fusion and internal fixation; tumor surgery, e.g., deficit filling; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay implantable matrices; implant placement and revision; sinus lifts; cosmetic procedures; etc. Specific bones that can be repaired or replaced with the implantable matrix herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and/or metatarsal bones.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A composition for augmenting bone formation, the composition comprising a matrix configured to allow growth of bone and/or cartilage, the matrix having a porosity between about 50% to about 70% and comprising stem cells, calcium ions, phosphate ions and demineralized bone matrix, the calcium ions being complexed to the phosphate ions as calcium phosphate ions, wherein the calcium and phosphate ions are available in a quantity to have a biological effect on the stem cells, and the calcium and phosphate ions are present in a ratio of about 1:5 to about 1:3 or about 5:1 to about 3:1.

2. A composition of claim 1, wherein the matrix is a porous ceramic.

3. A composition of claim 2, wherein the ceramic is in particulate form.

4. A composition of claim 2, wherein the ceramic is a structurally stable, three dimensional implant.

5. A composition of claim 1, wherein the calcium and phosphate ions have a biological effect on the stem cells upon implantation.

6. A composition of claim 1, wherein the calcium and phosphate ions are in a buffer solution used to deliver the stem cells to the matrix.

7. A composition of claim 1, wherein the stem cells are allogenic stem cells.

8. A composition of claim 1, further comprising pores wherein at least 30% of the pores are between about 50 micrometers and about 150 micrometers.

9. A composition of claim 1, wherein the matrix is implantable and the matrix comprises a diameter or diagonal of about 5 mm to about 10 mm.

10. A method of treating a bone defect in which a bone defect site possesses at least one cavity, said method comprising inserting a composition into the defect, the composition comprising a matrix configured to allow growth of bone and/or cartilage, the matrix having a porosity between about 50% and about 70% and comprising stem cells, calcium ions, phosphate ions and demineralized bone matrix, the calcium ions being complexed to the phosphate ions as calcium phosphate ions, wherein the calcium and phosphate ions are available in a quantity to have biological effect on the stem cells, and the calcium and phosphate ions are present in a ratio of about 1:5 to about 1:3 or about 5:1 to about 3:1, and wherein the matrix allows influx of at least one progenitor, bone, and/or cartilage cell therein.

11. A method according to claim 10, wherein the matrix further comprises bone morphogenic protein.

* * * * *